United States Patent
Shiotani et al.

(10) Patent No.: US 8,759,288 B2
(45) Date of Patent: Jun. 24, 2014

(54) BLASTOCYST CULTURE SUPERNATANT AS A FERTILITY AGENT IN BLASTOCYST TRANSFER

(71) Applicant: JCR Pharmaceuticals Co., Ltd., Hyogo (JP)

(72) Inventors: Masahide Shiotani, Hyogo (JP); Sakae Goto, Osaka (JP)

(73) Assignee: JCR Pharmaceuticals Co., Ltd., Ashiya-shi (JP)

( * ) Notice: Subject to any disclaimer, the term of this patent is extended or adjusted under 35 U.S.C. 154(b) by 18 days.

(21) Appl. No.: 13/626,271

(22) Filed: Sep. 25, 2012

(65) Prior Publication Data

US 2013/0023726 A1 Jan. 24, 2013

Related U.S. Application Data

(62) Division of application No. 12/376,167, filed as application No. PCT/JP2007/064961 on Jul. 31, 2007, now abandoned.

(30) Foreign Application Priority Data

Aug. 4, 2006 (JP) .................................. 2006-212797

(51) Int. Cl.
- *A61D 19/00* (2006.01)
- *A61B 17/435* (2006.01)
- *A61K 35/48* (2006.01)
- *C12N 5/073* (2010.01)
- *A61M 37/00* (2006.01)

(52) U.S. Cl.
USPC .............................. 514/9.8; 424/582; 600/33

(58) Field of Classification Search
None
See application file for complete search history.

(56) References Cited

U.S. PATENT DOCUMENTS

2005/0118661 A1 6/2005 Mardon
2005/0241013 A1 10/2005 Sher

FOREIGN PATENT DOCUMENTS

WO WO 2007012117 2/2007
WO WO 2007064961 9/2007

OTHER PUBLICATIONS

Goto et al., Fertility and Sterility, 2007; 88: 1339-1343.*
Pubmed documentation of an e-publication date of Jun. 7, 2007 for Goto et al. (Fertility and Sterility, 2007; 88: 1339-1343): one page total.*
Baranao, R.I. et al. "Determination of IL-1 and IL-6 Levels in Human Embryo Culture-Conditioned Media." (Am. J. Reprod. Endocrinol.), 1997, 191-194, 37.
De Los Santos, M.J. et al. "Expression of Interleukin-1 System Genes in Human Gametes." (Biol. Reprod.), 1998, 1419-1424, 59.
Edwards, R.G. and H.K. Beard. "Blastocyst stage transfer: pitfalls and benefits." (Hum. Reprod.), 1999, 1-4, 14:1.
Gardner, D.K. et al. "A prospective randomized trial of blastocyst culture and transfer in in-vitro fertilization." (Hum. Reprod.), 1998, 3434-3440, 13:12.
Gardner, D.K. et al. "Culture and transfer of human blastocysts increases implantation rates and reduces the need for multiple embryo transfers." (Fertil. Steril.) Jan. 1998, 84-88, 69:1.
Goto, S. "Symposium 5 'For Improvement of Disturbed Implantation—From Basics to Clinics.—'"(Journal of Reproductive Medicine), Oct. 1, 2006, 213, 51:4. (English Translation and Original Japanese Document).
Goto, S. "Improvement in Rates of Implantation and Pregnancy by Injection into the Uterine Cavity of Supernatant of the Culture of Embryos prior to Blastocyst Transfer—A New Method for Embryo Transfer Based on the Concept of Promotion of Embryo Receptivity by Embryos—." (Journal of Reproductive Medicine), Oct. 1, 2006, 276, 51:4. (English Translation and Original Japanese Document).
Goto, S. "Special Topic: For Improvement of Disturbed Implantation; 4. Method for Treatment 5.) Two-Step Embryo Transfer." (Obstet. Gynecol.) 2003, 1362-1367, 70:10. (English Translation and Original Japanese Document).
Giudice, L.C. "Endometrial Growth Factors and Proteins." (Seminars in Reproductive Endocrinology), May 1995, 93-101, 13:2.
Jurisicova, A. et al. "Variability in the expression of trophectodermal markers β-human chorionic gonadotrophin, human leukocyte antigen-G and pregnancy specific β-1 glycoprotein by the human blastocyst." (Hum. Reprod.), 1999, 1852-1858, 14:7.
Licht, P. et al. "On the Role of Human Chorionic Gonadotropin (hCG) in the Embryo-Endometrial Microenvironment: Implications for Differentiation and Implantation." (Seminars in Reproductive Medicine), 2001, 37-47, 19:1.
Liu, H.C. et al. "Production of Insulin-Like Growth Factor Binding Proteins (IGFBPs) by Human Endometrial Stromal Cells Is Stimulated by the Presence of Embryos." (J. Assist. Reprod. Genet.), 1995, 78-87, 12:2.
Milki, A.A. et al. "Two-blastocyst transfer has similar pregnancy rates and a decreased multiple gestation rate compared with three-blastocyst transfer." (Fertil. Steril.), Aug. 1999, 225-228, 72:2.

(Continued)

*Primary Examiner* — Bridget E Bunner
*Assistant Examiner* — Christina Borgeest
(74) *Attorney, Agent, or Firm* — Millen, White, Zelano & Branigan, P.C.

(57) ABSTRACT

Means for improving the success rate of pregnancy on the basis of blastocyst transfer is disclosed. The means comprises an agent for promoting pregnancy in blastocyst transfer comprising the supernatant of the culture which is obtained by culturing a human embryo in a medium until the embryo develops into a blastocyst. Also disclosed are a method for production of the agent, as well as a method for promoting pregnancy comprising; culturing a human embryo in a medium until the human embryo develops into a blastocyst, injecting a composition comprising the supernatant of the culture into the uterine cavity of a patient who is to undergo blastocyst transfer, and then transferring the blastocyst to the recipient.

11 Claims, No Drawings

(56) References Cited

OTHER PUBLICATIONS

Perrier D'Hauterive, S. "Human chorionic gonadotropin and growth factors at the embryonic-endometrial interface control leukemia inhibitory factor (LIF) and interleukin 6 (IL-6) secretion by human endometrial epithelium." (Hum. Reprod.), 2004, 2633-2643, 19:11.

Scholtes, M.C.W. "Blastocyst transfer in day-5 embryo transfer depends primarily on the number of oocytes retrieved and not on age." (Fertil. Steril.), Jan. 1998, 78-83, 69:1.

Sheth K.V. et al. "Prediction of successful embryo implantation by measuring interleukin-1-alpha and immunosuppressive factor(s) in preimplantation embryo culture fluid." (Fertil. Steril.), May 1991, 952-957, 55:5.

Simon, C. et al. "Embryonic Regulation of Integrins βa, α4, and α1 in Human Endometrial Epithelial Cells in Vitro." (J. Clin. Endocrinol. Metab.), 1997, 2607-2616, 82.

Tazuke, S. and L.C. Giudice. "Growth Factors and Cytokines in Endometrium, Embryonic Development, and Maternal: Embryonic Interactions." (Seminars in Reproductive Endocrinology), Aug. 1996, 231-245, 14:3.

Wakuda, K. et al. "Embryo-dependent induction of embryo receptivity in the mouse endometrium." (J. Reprod. Fertil.), 1999, 315-324, 115.

Watson, E.D. "Suppression of Lymphocyte Reactivity by Culture Supernatant from Horse Embryos and Endometrium." (Biol. Reprod.), 1990, 294-300, 42.

Menezo et al., Fertility and Sterility, 1992; 58:977-980.

Dunglison et al., Human Reprod. 1996; 11:191-196.

Mayumi et al., J. Immunol. 1985; 134:404-409.

Behr et al., Human Reprod., 1999; 14:454-457.

Kovacic et al., Fertility and Sterility; 2002; 77:529-536.

Gardner & Lane, Human Reproduction Update 1997; 3:367-382.

Lane & Gardner, Hum. Reprod. 1992; 7:558-562.

Goto et al., Fertility and Sterlity, 2007; 88:1330-1343.

\* cited by examiner

BLASTOCYST CULTURE SUPERNATANT AS A FERTILITY AGENT IN BLASTOCYST TRANSFER

This application is a divisional of Ser. No. 12/376,167, filed Feb. 3, 2009 (now abandoned), which is a 371 US national phase application of International Application PCT/JP2007/064961, filed Jul. 31, 2007, which claim the benefit of priority of Japanese Application No. 2006-212797, filed Aug. 4, 2006.

FIELD OF THE INVENTION

The present invention relates to a composition which promotes pregnancy in human fertility treatment by blastocyst transfer, a method for production of the composition, as well as a method for promoting pregnancy in a human who undergoes blastocyst transfer.

BACKGROUND OF THE INVENTION

In humans, infertility is said to be observed around 10% of couples. Therefore, there have been substantial needs for fertility treatment, and by now, it is a common practice. Among different procedures of fertility treatment, those in which sperm cell or eggs are directly handled are known as artificial insemination and in vitro fertilization, respectively. Artificial insemination is a technique to promote pregnancy by injecting sperm cells into the vagina at a position close to the cervix, or directly into the uterus or the oviducts, using an instrument such as catheter and the like, and it aims to increase the success rate of fertilization by avoiding obstacles that sperm cells might encounter until they could meet an egg. On the other hand, in vitro fertilization is a technique by which a patient is administered a fertility drug to induce generation of ova, which then are collected out of the body and mixed with sperm cells in a test tube (insemination) to have them got fertilized, and the fertilized eggs then are cultured and, on day 2 or 3 of culture in general, embryos at 4- or 8 cell stage are transferred into the uterine cavity in general, with a catheter. In order to make the implantation of the transferred embryos easier, administration of luteinizing hormone is usually conducted in order to condition the uterine endometrium.

A preimplantation embryo produces several factors during its development to signal its presence to the maternal organism. Interleukin-1 (IL-1), for example, is a primary factor which modulates cross talks between the embryo and the uterine endometrium of the maternal organism, and a complete IL-1 system is found in a human embryo at all the stages of its development (see Non-patent Document 1). With regard to human chorionic gonadotropin (HCG), another one of the factors released by an embryo, the transcription of its gene can be found to occur already in a 2-cell stage embryo (see Non-patent Document 2). It also is observed that several embryonic factors, including the above factors, involved in the cross talks are released out of the cell when it is cultured in vitro (in a test tube). Namely, several embryonic factors that modulate endometrial receptivity are detectable in the supernatant of embryo cultures (see Non-patent Documents 3-9). It also is known that, in vivo, an embryo developing in the oviduct induces differentiation of the uterine endometrium (see Non-patent Document 10). All these facts, taken together, indicate that the cross talks are brisk at the early stages of embryonic development, between the embryo and the uterine endometrium via the factors produced by the embryo. In fact, it has been shown that not only a preimplantation embryo in the uterine cavity, but also even an early embryo still remaining in the oviduct has the ability to modulate certain molecules in the uterine endometrium to place its implantation under its own control (see Non-patent Document 10).

In recent years, blastocyst transfer, a new technique of in vitro fertilization, has been proposed and practiced clinically as a means of improving the success rate of implantation in human fertility treatment (see Non-patent Documents 11-13). In this technique, embryos produced by in vitro fertilization as described above are cultured for 5 to 6 days to let them develop into blastocysts and then injected into the uterine cavity. Employing the technique of blastocyst transfer, higher implantation rates result compared with the transfer of embryos at earlier stages, for the former allows physiological synchronization of the uterine endometrium with the developmental stage of the embryos, as well as relatively easier selection of embryos with higher ability for implantation owing to a longer in vitro culture (see Non-patent Documents 14 and 15). That the number of days required for implantation to occur after blastocyst transfer is as short as 1 day, in contrast with the 4-5 days required with 2-3 day-cultured embryos, reduces the risk of washout of embryos out of the uterus, and is therefore beneficial to implantation. Even so, however, the success rate of pregnancy by human blastocyst transfer actually remains at a low level of about 36.4%. Unsuccessful implantation after blastocyst transfer is thought to be due, e.g., to failure of the blastocyst to escape from the zona pellucida or to arrested development of the transplanted blastocyst in the uterine cavity. Thus, as there is still a majority of cases where blastocyst transfer fails to achieve pregnancy, further means is needed to increase the success rate of achieving pregnancy.

[Non-patent Document 1] De los Santos M J, Anderson D J, Racowsky C, Simon C, and Hill J A (1998) Biol Reprod. 59, 1419-1424

[Non-patent Document 2] Jurisicova A, Antenos M, Kapasi K, Meriano J, and Casper R F (1999) Hum Reprod. 14, 1852-1858

[Non-patent Document 3] Tazuke S I, and Giudice L C, (1996) Semin Reprod Endocrinol. 14, 231-245

[Non-patent Document 4] Simon C, Gimeno M J, Mercader A, O'Connor J E, Remohi J, Polan M L, and Pellicer A (1997) J Clin Endocrinol Metab. 82, 2607-2616

[Non-patent Document 5] Giudice L C (1995) Semin Reprod Endocrinol. 13, 93-101

[Non-patent Document 6] Sheth K V, Roca G L, al-Sedairy S T, Parhar R S, Hamilton C J, and al-Abdul Jabbar F (1991) Fertil Steril. 55, 952-957

[Non-patent Document 7] Baranao R I, Piazza A, Rumi L S, and Polak de Fried E (1997) Am J Reprod Immunol. 37, 191-194

[Non-patent Document 8] Licht P, Russu V, and Wildt L (2001) Semin Reprod Med. 19, 37-47

[Non-patent Document 1] Perrier d'Hauterive S, Charlet-Renard C, Berndt S, Dubois M, Munaut C, Goffin F, et. al. (2004) Hum Reprod. 19, 2633-2643

[Non-patent Document 10] Wakuda K, Takakura K, Nakanishi K, Kita N, Shi H, Hirose M, and Noda Y (1999) J Reprod Fertil. 115, 315-324

[Non-patent Document 11] Gardner D K, Schoolcraft W B, Wagley L, Schlenker T, Stevens J, and Hesla J A (1998) Hum Reprod. 13, 3434-3440

[Non-patent Document 12] Scholtes M C, and Zeilmaker G H (1998) Fertil Steril. 69, 78-83

[Non-patent Document 13] Milki A A, Fisch J D, and Behr B (1999) Fertil Steril. 72, 225-228

[Non-patent Document 14] Gardner D K, Vella P, Lane M, Wagley L, Schlenker T, and Schoolcraft W B (1998) Fertil Steril. 69, 84-88

[Non-patent Document 15] Edwards R G, and Beard H K (1999) Hum Reprod. 14, 1-4

SUMMARY OF THE INVENTION

On the basis of the technique of blastocyst transfer, by which the rate of achieving pregnancy still remains at about 36.4%, the objective of the present invention is to provide a means to increase the success rate of achieving pregnancy.

The present inventors assumed that the lack of cross talks between the uterine endometrium and the embryos at the stage of development from earlier embryos to blastocysts is a factor causing unsuccessful blastocyst transfer. This lack of cross talks could cause insufficient modulation of the endometrial receptivity to embryos. Thus, the present inventors pursued investigations to increase the success rate of implantation and pregnancy in human blastocyst transfer, focusing on the modulation of the endometrial receptivity by embryos. Having attempted blastocyst transfer after injecting in advance culture supernatant of human embryos into the uterine cavity of a recipient, the present inventors found that implantation and pregnancy was achieved with higher success rate than achieved by conventional blastocyst transfer. In the technique of blastocyst transfer, there has been no report known to us as to increasing the success rate of implantation and pregnancy by injecting culture supernatant of embryos in advance into the uterus. The present invention was completed based on the finding and further studies thereupon.

Thus, the present invention provides what follows.

1. An agent for promoting pregnancy in blastocyst transfer comprising the supernatant of culture obtained by culturing a human embryo in a medium until the embryo develops into a blastocyst.

2. The agent for promoting pregnancy according to 1 above, wherein the supernatant of culture is obtained from the medium in which the human embryo has been cultured for at least 2 days.

3. The agent for promoting pregnancy according to 1 or 2 above, wherein the culture has been carried out in 10-100 µL of the medium per human embryo.

4. The agent for promoting pregnancy according to one of 1 to 3 above comprising a portion of the culture supernatant allotted to at least 0.3 embryo.

5. The agent for promoting pregnancy according to one of 1 to 4 above, wherein the medium is a serum-free medium.

6. A method for production of an agent for promoting pregnancy in blastocyst transfer comprising the steps of;
   culturing a human embryo in a medium to let the embryo develop into a blastocyst, and
   collecting the supernatant of the medium of the culture in which the blastocyst is formed.

7. The method for production of an agent for promoting pregnancy according to 6 above, wherein the culture is carried out for at least 2 days.

8. The method for production of an agent for promoting pregnancy according to 6 or 7 above, wherein the culture is carried out in 10-100 µL of the medium per human embryo.

9. The method for production of an agent for promoting pregnancy according to one of 6 to 8 above, wherein the culture supernatant in an amount corresponding to at least 0.3 human embryo is collected.

10. The method for production of an agent for promoting pregnancy according to one of 6 to 9 above, wherein the medium is a serum-free medium.

11. A method for promoting pregnancy in a human comprising the following steps of;
   culturing a human embryo in a medium until the human embryo develops into a blastocyst,
   injecting a composition comprising the supernatant of the culture into the uterine cavity of a human patient who is to undergo blastocyst transfer, and
   transferring one or more blastocyst into the uterine cavity of the patient.

12. The method according to 11 above, wherein the culture is carried out for at least 2 days.

13. The method according to 11 or 12 above, wherein the culture is carried out in 10-100 µL of the medium per human embryo.

14. The method according to one of 11 to 13 above, wherein the culture supernatant in an amount corresponding to at least 0.3 human embryo is collected.

15. The method according to one of 11 to 14 above, wherein the medium is a serum-free medium.

16. The method according to one of 11 to 15 above, wherein the injection of the composition is done 1-5 days before the transfer of the blastocyst.

When injected into the uterine cavity prior to the transfer of a blastocyst into the uterus of the human recipient of an embryo, the pregnancy promoting agent according the present invention as described above remarkably increases the success rate of implantation of a transplanted blastocyst and pregnancy, compared with conventional blastocyst transfer.

BEST MODE FOR CARRYING OUT THE INVENTION

The present inventors assume that the marked improvement in the success rate of implantation and pregnancy in blastocyst transfer according to the present invention is due to the establishment of an optimal circumstance for transferred blastocyst, by stimulating the uterine endometrium with administered supernatant containing embryo-derived factors which, having been released from the embryo, modulate the endometrium receptivity. Therefore, we think that the improvement in the success rate of implantation and pregnancy brought about by the present invention is owing to supplementation, with the embryo-derived factors in the medium administered prior to blastocyst transfer, of communication, which would have been present between the uterine endometrium and the embryo at the stage of development from an earlier embryo to a blastocyst, the communication which is never provided in conventional blastocyst transfer.

The pregnancy promoting agent of the present invention is a composition comprising the supernatant of a culture obtained by culturing one or more human embryos in a medium until they develop into blastocysts (e.g., culture supernatant itself). The supernatant of a culture to be collected is preferably that in which at least 2-day, more preferably 3-day culture was performed before collection. A medium to be employed may be any of conventional media conventionally used in blastocyst transfer. A serum-free medium is preferred considering that the risk of contamination with prion or other infectious agents should be eliminated. Examples of such serum-free media at present include BLASTASSIST® System media 1 and 2, in particular BLASTASSIST® System medium 2 (MediCult, Jyllinge, Denmark) which can be used suitably in the culture to be continued for some three days until blastocysts are formed.

Considering both the necessity of supplying a sufficient amount of a medium to blastocysts and the convenience for collecting the blastocysts from the medium, the above-mentioned culture of human embryos is conducted preferably in an amount to the medium which corresponds to 10-100 µL of the medium per human embryo, and more preferably in 10-60 µL of the medium per human embryo.

It is preferred that the agent of the present invention comprises the culture supernatant in an amount corresponding to a potion allotted to at least 0.3 embryo out of the total amount of the culture in which blastocysts have developed. Namely, in the case where only one embryo is cultured in 50 µL of the medium until it develops into a blastocyst, it is preferred that 15 µL of the supernatant (i.e., 50 µL×0.3) collected from the medium is contained in the composition according to the present invention. However, as it is allowed to divide the supernatant into aliquots in smaller units for storage, and combine two or more of them in use (when injection is made into a patient), it is not always necessary, in such a case, that a unit amount of the composition should contain a portion of the culture medium allotted to at least 0.3 embryo.

The collected culture supernatant may be used directly, or frozen-stored and thawed before use. It is also allowed to add one or more pharmaceutically inert diluents (e.g., sterile purified water, or aqueous solution containing human plasma albumin, glucose, sodium chloride and the like, which are compounds contained in BLASTASSIST® System medium 2 as described in the section of Examples) to increase the volume by dilution into a volume which is easier to handle, e.g., 0.2 mL or 0.5 mL.

The pregnancy promoting agent according to the present invention in injected into the uterine cavity of a recipient prior to the transfer of blastocysts into her uterus in a blastocyst transfer procedure. Though the recipient of the blastocysts is in usual cases the very donor of the ova from which the embryos have developed, the recipient also may be a different individual. Therefore, the recipient of the pregnancy promoting agent according to the present invention may also be either the donor of the ova from which the embryos have developed, or a different individual. Also, it is allowed to frozen-store separately and portionwise, for example, the supernatant of the culture of a number of embryos, and thaw and inject a potion of it into different recipients' uterine cavity prior to the transfer of the blastocysts carried out using different blastocysts.

The pregnancy promoting agent according to the present invention is injected into the uterine cavity of a patient preferably 1-5 days before, more preferably 2-4 days before the transfer of blastocysts is carried out. Injection may be once (e.g., once, 3 days before) or repeated multiple times every other day or even everyday.

The present invention also provides a method for promoting pregnancy in a human comprising; culturing a human embryo in a medium until the human embryo develops into a blastocyst, injecting a composition comprising the supernatant of the culture (e.g., the culture supernatant itself) into the uterine cavity of a human recipient who is to undergo blastocyst transfer, and then transferring the blastocyst into the uterine cavity of the recipient. Wherein, the injection of the composition is done preferably 1-5 days, more preferably 2-4 days, and particularly preferably 3 days before the transfer of the blastocyst.

When injected into the uterine cavity prior to the transfer of a blastocyst into the uterus of a recipient, the pregnancy promoting agent according to the present invention remarkably increases the success rate of implantation and pregnancy in blastocyst transfer.

EXAMPLES

While the present invention is described in further detail below with reference to an example, it is not intended that the present invention be limited to the example.

[Test Protocol]

Twenty-two patients were enrolled. The patients, under a hormone replacement therapy (HRT) with estrogen and progesterone, received the transfer of frozen-thawed blastocysts during the period between January, 2005 and April, 2006. The criteria of patients to be included in the study were that they were at least 32 years of age, had a history of one or more unsuccessful blastocyst transfer or two-step (consecutive double) embryo transfer, and that they had at least four early embryos on day 2 in oocytes retrieval cycles.

In the previous treatment cycle, the patients were treated with a long protocol. Briefly, the patients started to receive 600 µg of a gonadotropin-releasing hormone (GnRH) agonist on day 7 of the hyperthermic phase in the cycle of treatment, and then, on day 3 of menstruation and thereafter, received daily stimulation of ovaries with follicle-stimulating hormone (FSH preparation or HMG preparation) until the size of the second leading follicle reached 18 mm in diameter. Ovulation was triggered when the second leading follicle became greater than 18 mm in diameter. Ova were retrieved transvaginally under utrasonographic guidance 36 hours after intramuscular injection of 500 units of human chorionic gonadotropin (hCG). The follicles were measured by ultrasonic scanning (Mitsubishi RDF173H).

The ova thus retrieved were fertilized by insemination or intracytoplasmic sperm injection. The fertilized eggs were cultured in a 50-1 µL droplet of BLASTASSIST® System medium 1 [containing synthetic serum replacement (SSR), human plasma albumin, glucose, sodium pyruvate, lactate, potassium sulfate, magnesium sulfate, sodium chloride, sodium hydrogen phosphate, non-essential amino acids, L-glutamine, taurine, sodium bicarbonate, HEPS, streptomycin 50 mg/L, penicillin 50,000 IU/L, and phenol red: MediCult, Jyllinge, Denmark] and early embryos were obtained on day 2. Then, one to four of the early embryos thus obtained were cultured in a 50-1 µL droplet of BLASTASSIST® System medium 2 [containing synthetic serum replacement (SSR), human plasma albumin, glucose, sodium pyruvate, lactate, potassium sulfate, magnesium sulfate, sodium chloride, sodium hydrogen phosphate, essential amino acids, non-essential amino acids, L-glutamine, taurine, sodium bicarbonate, streptomycin 50 mg/L, penicillin 50,000 IU/L, and phenol red: MediCult, Jyllinge, Denmark], i.e., in 12.5-50 µL of the medium per embryo, under a covering layer of mineral oil (Oil Embryo Culture, Irvine Scientific Santa Ana Calif. USA) for further three days, i.e., up to day 5 in total, to obtain blastocysts. The culture plates employed here were FALCON353002 Tissue Culture Dishes (Becton Dickinson, Franklin Lakes USA. The culture of the embryos were carried out in an incubator (TE-HER PRODUCT $O_2.CO_2$ incubator CP O2-1800, Hirasawa, Tokyo, Japan) set at 5% $CO_2$, 5% $O_2$, 90% $N_2$ 37° C., and 100% humidity. The fresh early embryos and a part of the blastocysts obtained by the culture were directly used for transplantation in the previous treatment cycle, and the other blastocysts, which were not used for transplantation in the cycle, were frozen-stored. The supernatant of the embryo culture in BLASTASSIST® System medium 2 was frozen-stored at −20° C.

In the previous treatment cycle, the patients underwent the transfer of early embryos which were obtained by the above culture on day 2 after ova retrieval, and blastocysts obtained by the above culture on day 5 after oval retrieval, respectively. Patients who got pregnant by this pretreatment dropped out of the study.

The patients (22) who failed to get pregnant by the transplantation in the previous treatment cycle received the following treatment in the first menstruation cycle after the transplantation, as well as in the second menstruation cycle. Application of Estraderm M, an estradiol preparation, was started on day 2 of the menstruation cycle. Two sheets of Estraderm M were applied every other day while gradually increasing the number applied in such a manner as three sheets on day 10, four sheets on day 12, and 6 sheets on day 14, and thereafter three sheets from day 16 to 30, which is the day when pregnancy was tested. From day 15 of the menstruation cycle, administration of a progesterone vaginal suppository (400 mg/day) as a progesterone preparation was started together with chlorpromazine acetate 12 mg/day (p.o.).

On day 20 of the hormone replacement therapy (HRT) cycle, one or two blastocysts were transferred to each patient. This was performed transcervically using a fai con IVF catheter (Fuji systems).

In the Stimulation of Endometrium Embryo Transfer (SEET) group, the frozen-stored supernatant of the culture of patient's own embryos in BLASTASSIST® System medium 2 was thawed and 20 μL of it was administered into the uterine cavity of each of 11 patients prior to blastocyst transfer on day 17 of the hormone replacement therapy (HRT) cycle. The administration was carried out using a fai con IVF catheter (Fuji Systems) which was loaded with 20 μL of the supernatant of the embryo culture and inserted in the cervical canal, and by releasing the supernatant when the tip of the catheter was about 1 mm from the fundus of the uterine cavity Eleven patients who were assigned to the control, a conventional blastocyst transfer group (BT group), underwent blastocyst transfer without receiving the supernatant of the embryo culture in the uterine cavity.

On day 17 after the transfer of the embryos, ultrasonic scanning (Mitsubishi RDF173H) was performed to examine for a gestational sac in the uterine cavity.

[Groups Tested]

The basic characteristics of the patient of SEET and BT groups are shown in Table 1. The average age (±SD) of the patients in SEET and BT groups was 37.1±4.1 years and 36.0±3.4 years (p=0.47), respectively. The duration of infertility (±SD) was 7.6±3.8 years in SEET group and 6.0±2.3 years in BT group (p=0.27). The number of previous assisted reproductive technology (ART) cycles, such as in vitro fertilization, experienced by the patients before the present test was 1.6±0.9 in SEET group and 2.5±2.9 in BT group (p=0.39). Basal level (±SD) of follicle-stimulating hormone (FSH) was 6.5±2.0 mIU/mL in SEET group and 5.7±2.7 mIU/mL in BT group (p=0.46). The number (±SD) of ova fertilized was 8.5±2.0 in SEET group and 8.5±1.7 in BT group (p=1.0). The number (±SD) of the blastocysts transferred was 1.5±0.5 in SEET group and 1.5±0.5 in BT group (p=0.69). As shown above, there was no significant difference in the basic characteristics between SEET and BT groups. Further, the quality of transferred blastocysts was comparable between the two groups.

[Results] The Efficacy and Safety of SEET

The results are presented in Table 1. While 10 out of the 11 patients did get pregnant in SEET group, only 4 out of the 11 patients got pregnant in BT group. The rate of pregnancy (the percentage (%) of the patients in whom gestational sac formed) was 91.9% SEET group and 36.4% in BT group, indicating statistically significant improvement (p=0.027) in the pregnancy rate in SEET group compared with BT group. The implantation rate (the percentage (%) of the transferred blastocysts which developed into gestational sacs) was 70.6% in SEET group and 25.0% in BT group, indicating statistically significant improvement (p=0.023) in the implantation rate in SEET group compared with BT group. No side effect was observed in either of the groups.

TABLE 1

|  | SEET group | BT group | Significance (p) |
| --- | --- | --- | --- |
| Age of patients (mean ± SD) | 37.1 ± 4.1 | 36.0 ± 3.4 | 0.47 |
| Duration of infertility (year) (mean ± SD) | 7.6 ± 3.8 | 6.0 ± 2.3 | 0.27 |
| Number of previous assisted reproductive technology cycles | 1.6 ± 0.9 | 2.5 ± 2.9 | 0.39 |
| Basal FSH levels (mIU/mL) (mean ± SD) | 6.5 ± 2.0 | 5.7 ± 2.7 | 0.46 |
| Number of ova fertilized (mean ± SD) | 8.5 ± 2.0 | 8.5 ± 1.7 | 1 |
| Number of blastocysts transferred (mean ± SD) | 1.5 ± 0.5 | 1.5 ± 0.5 | 0.69 |
| Number of clinical events of pregnancy | 10 | 4 | — |
| Rate of pregnancy per transfer procedure (%) | 91.9 | 36.4 | 0.027 |
| Rate of implantation per embryo (%) | 70.6 | 25.0 | 0.023 |

INDUSTRIAL APPLICABILITY

The present invention is useful as a new type of pregnancy promoting agent which remarkably improves the success rate of pregnancy and implantation in blastocyst transfer.

What is claimed is:

1. A method for promoting pregnancy in a human comprising:
   culturing a human embryo in a medium until the human embryo develops into a blastocyst,
   injecting a composition comprising the supernatant of the culture into the uterine cavity of a human patient who is to undergo blastocyst transfer, wherein the injection of the composition is done 1-5 days before the transfer of the blastocyst, and
   transferring a blastocyst into the uterine cavity of the patient.

2. The method according to claim 1, wherein the culture is carried out for at least 2 days.

3. The method according to claim 2, wherein the culture is carried out in 10-100 μL of the medium per human embryo.

4. The method according to claim 2, wherein the composition comprises a portion of the culture supernatant allotted to at least 0.3 of the human embryo.

5. The method according to claim 2, wherein the medium is a serum-free medium.

6. The method according to claim 1, wherein the culture is carried out in 10-100 μL of the medium per human embryo.

7. The method according to claim 6, wherein the composition comprises a portion of the culture supernatant allotted to at least 0.3 of the human embryo.

8. The method according to claim 6, wherein the medium is a serum-free medium.

9. The method according to claim 1, wherein the composition comprises a portion of the culture supernatant allotted to at least 0.3 of the human embryo.

10. The method according to claim 9, wherein the medium is a serum-free medium.

11. The method according to claim 1, wherein the medium is a serum-free medium.

* * * * *